United States Patent
Watanabe et al.

(10) Patent No.: US 10,618,862 B2
(45) Date of Patent: *Apr. 14, 2020

(54) PROCESS FOR PREPARING (9E, 11Z)-9,11-HEXADECADIENAL

(71) Applicant: SHIN-ETSU CHEMICAL CO., LTD., Tokyo (JP)

(72) Inventors: Tomohiro Watanabe, Niigata (JP); Yuki Miyake, Niigata (JP); Takeshi Kinsho, Niigata (JP); Yusuke Nagae, Niigata (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/388,124

(22) Filed: Apr. 18, 2019

(65) Prior Publication Data

US 2019/0322605 A1  Oct. 24, 2019

(30) Foreign Application Priority Data

Apr. 18, 2018 (JP) ................. 2018-079750

(51) Int. Cl.
*C07C 29/58* (2006.01)
(52) U.S. Cl.
CPC ................. *C07C 29/58* (2013.01)
(58) Field of Classification Search
CPC .................................................. C07C 29/58
See application file for complete search history.

(56) References Cited

U.S. PATENT DOCUMENTS 4,357,474 A  11/1982  Carney et al.

FOREIGN PATENT DOCUMENTS

EP   3 392 231 A1   10/2018

OTHER PUBLICATIONS

Harris, M.K. et al., *A New Pheromone Race of Acrobasis muxvorella (Lepidoptera: Pyralidae)*, Journal of Economic Entomology, vol. 101, No. 3 (2008) 769-776.

Millar, J. G. et al., *Sex Attractant Pheromone of the Pecan Nut Casebearer (Lepidoptera: Pyralidae)*, Bioorganic & Medicinal Chemistry, vol. 4, No. 3 (1996) 331-339.

Extended European Search Report for Application No. EP 19167827.5 dated Jun. 18, 2019, 6 pages.

Tao, Y. et al., *Facile Synthesis of (Z,E)-9,11-Hexadecadienal, the Major Sex Pheromone Component of the Sugarcane Borer Diatrea Saccharalis: An Efficient Strategy for Synthesis of (Z,E)-Dienic Pheromone*, Synthetic Communication® 43 (2013) 415-424.

*Primary Examiner* — Sikarl A Witherspoon
(74) *Attorney, Agent, or Firm* — Rimon, P.C.

(57) ABSTRACT

An efficient process for preparing (9E,11Z)-9,11-hexadecadienal of formula (4)

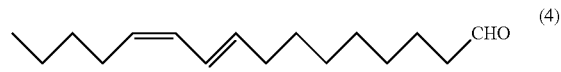

is provided. The process includes at least steps of: conducting a nucleophilic substitution reaction between an (8E, 10Z)-8,10-pentadecadienyl magnesium halide derived from an (8E,10Z)-1-halo-8,10-pentadecadiene of (1):

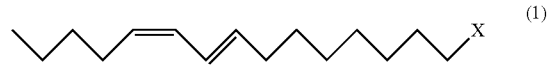

and an orthoformate ester (2)

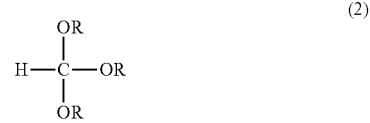

to thereby prepare a (9E, 11Z)-1,1-dialkoxy-9, 11-hexadecadiene (3):

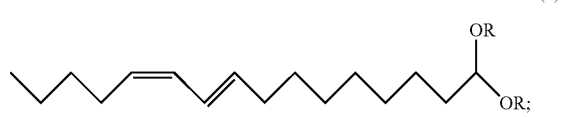

and hydrolyzing the (9E, 11Z)-1,1-dialkoxy-9,11-hexadecadiene (3) to obtain (9E, 11Z)-9,11-hexadecadienal (4).

2 Claims, No Drawings

PROCESS FOR PREPARING (9E, 11Z)-9,11-HEXADECADIENAL

FIELD

The present invention relates to a process for preparing (9E,11Z)-9,11-hexadecadienal.

BACKGROUND

Pecan nut casebearer (*Acrobasis nuxvorella*) is a serious insect pest against pecans, which tunnels into pecan nuts and feeds in the nuts. The use of insecticides for pest control on the pecan nut casebearer may lead to outbreak of secondary insect pests, such as aphids, mites and leaf-miner flies, because the insecticides also kill natural enemies of such secondary insect pests. Therefore, a large hope is placed on mating disruption using a sex pheromone.

(9E,11Z)-9,11-Hexadecadienal and (9E,11Z)-9,11-hexadecadienyl acetate were identified as components of natural sex pheromones of the pecan nut casebearer (Non-Patent Literatures 1 and 2).

Millar et al. describes a process for preparing (9E,11Z)-9,11-hexadecadienal, in which a vinyl iodide derived from 9-decyn-1-ol is subjected to the Sonogashira coupling with 1-hexyne, followed by alcohol protection, hydroboration and subsequent protonation, removal of a protecting tetrahydropyranyl (THP) group for the hydroxy group, and oxidation (Non-Patent Literature 1). Harris et al. describes another process for preparing (9E,11Z)-9,11-hexadecadienal, in which (1E)-1-chloro-1-octen-3-yne, which has been obtained by the Sonogashira coupling of (E)-1,2-dichloroethene with 1-hexyne, is subjected to the Kochi-Fürstner coupling with 1-(tetrahydropyranyloxy)-8-bromooctane derived from 1,8-octanediol to obtain (9E)-1-(tetrahydropyranyloxy)-9-hexadecen-11-yne, followed by hydroboration and subsequent protonation, removal of a protecting THP group, and oxidation (Non-Patent Literature 2).

SUMMARY

However, the process described in Non-Patent Literature 1 (J. G. Millar et al., Bioorg. Med. Chem. 1996, 4, 331-339) requires expensive catecholborane for the hydroboration, and expensive dichlorobis(triphenylphosphine) palladium for the Sonogashira coupling. Because an unstable vinyl iodide is used as an intermediate, the process is unsuitable for the industrial production. Further, the Swern oxidation is carried out at −78° C., so that it cannot be carried out in a usual reaction facility. The process is accompanied with heavy environmental burden, due to the generation of toxic carbon monoxide gas and stinking dimethyl sulfide. The process described in Non-Patent Literature 2 (M. K. Harris et al., J. Econ. Entomol. 2008, 101, 769-776) is also unsuitable for mass production in an industrial scale, because it requires expensive (E)-1,2-dichloroethene as a starting material and expensive dichlorobis(triphenylphosphine) palladium for the Sonogashira coupling as in Non-Patent Literature 1, and also because it is accompanied with heavy environmental burden due to the use of chromium for the oxidation.

Further, because a THP group is used as a protecting group in both of the processes of Non-Patent Literatures 1 and 2, two additional steps are required for the protection and deprotection of a hydroxy group. This is undesirable for industrial practice, because of the increased number of steps. Furthermore, the deprotection from an ether-type protecting group such as a THP group is an equilibrium reaction, so that some of the protection remains even after the deprotection step, which may lead to a decreased yield.

In addition, because the aldehyde is synthesized by the oxidation, the subsequent post-treatment and purification procedures may be laborious, making it difficult to isolate the aldehyde with a good yield. For example, the overall yield of (9E,11Z)-9,11-hexadecadienal is significantly so low as 29% in Non-Patent Literature 1, and 18% in Non-Patent Literature 2.

The present invention has been made in these circumstances, and aims to provide an efficient process for preparing (9E,11Z)-9,11-hexadecadienal from an (8E,10Z)-8,10-pentadecadienyl magnesium halide derived from an (8E,10Z)-1-halo-8,10-pentadecadiene.

As a result of intensive researches, the present inventors have found that (9E,11Z)-9,11-hexadecadienal can be produced with a high yield and a high purity, without using any protection or oxidation reaction, by using an (8E,10Z)-8,10-pentadecadienyl magnesium halide, i.e., a Grignard reagent, prepared from (8E,10Z)-1-halo-8,10-pentadecadiene, which can be produced in a large amount in an inexpensive way, and thus have completed the present invention.

According to one aspect of the invention, there is provided a process for preparing (9E,11Z)-9,11-hexadecadienal of the following formula (4):

the process comprising at least steps of:
conducting a nucleophilic substitution reaction between an (8E,10Z)-8,10-pentadecadienyl magnesium halide derived from an (8E,10Z)-1-halo-8,10-pentadecadiene of the following general formula (1):

wherein X is a halogen atom, and an orthoformate ester of the following general formula (2):

wherein R may be the same or different at each occurrence and is an alkyl group having 1 to 6 carbon atoms, to thereby prepare a (9E,11Z)-1,1-dialkoxy-9,11-hexadecadiene of the general formula (3):

wherein R may be the same or different at each occurrence and is an alkyl group having 1 to 6 carbon atoms; and hydrolyzing the (9E,11Z)-1,1-dialkoxy-9,11-hexadecadiene (3) to obtain (9E,11Z)-9,11-hexadecadienal of the formula (4) shown above.

According to the invention, (9E,11Z)-9,11-hexadecadienal, sex pheromone of the pecan nut casebearer with less environmental burden, can be produced with a high yield and a high purity, without using expensive reagents or any protection or oxidation reaction, and, therefore, without a need to use any special facility.

DETAILED DESCRIPTION

The inventors considered that an (8E,10Z)-1-halo-8,10-pentadecadiene of the general formula (1) could be obtained by a coupling reaction of an alkadienyl magnesium halide prepared from a 1-haloalkadiene of the general formula (5-2) with a dihaloalkane of the general formula (6-2), as shown below.

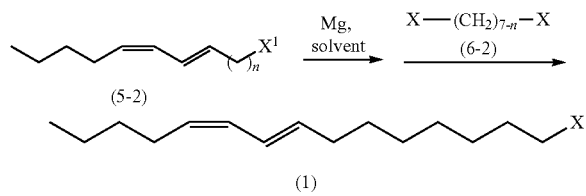

In the general formula (5-2) for the 1-haloalkadienes, $X^1$ is a halogen atom, examples of which preferably include chlorine, bromine and iodine atoms, and n is an integer of from 1 to 6. In the general formula (6-2) for the dihaloalkanes, X may be the same or different at each occurrence and is a halogen atom, examples of which preferably include chlorine, bromine and iodine atoms.

Possible combinations of the 1-haloalkadiene (5-2) and the dihaloalkane (6-2) include a (2E,4Z)-1-halo-2,4-nonadiene and a 1,6-dihalohexane (n=1), a (3E,5Z)-1-halo-3,5-decadiene and a 1,5-dihalopentane (n=2), a (4E,6Z)-1-halo-4,6-undecadiene and a 1,4-dihalobutane (n=3), (5E,7Z)-1-halo-5,7-dodecadiene and a 1,3-dihalopropane (n=4), (6E,8Z)-1-halo-6,8-tridecadiene and 1a,2-dihaloethane (n=5), and a (7E,9Z)-1-halo-7,9-tetradecadiene and a dihalomethane (n=6).

However, in a case where n=1, we thought it to be difficult to obtain the (8E,10Z)-1-halo-8,10-pentadecadiene (1) with a good yield, because a (2E,4Z)-2,4-nonadienyl magnesium halide prepared from the (2E,4Z)-1-halo-2,4-nonadiene is an allylic Grignard reagent, which is expected to cause dimerization. In a case where n=2, there is not established a good method to efficiently produce the (3E,5Z)-1-halo-3,5-decadiene with a high yield. In a case where n=5, we thought it to be difficult to obtain the (8E,10Z)-1-halo-8,10-pentadecadiene (1), because an elimination reaction prevails, rather than the desired coupling reaction, between the 1,2-dihaloethane with the Grignard reagent. In a case where n=6, we thought it to be difficult to obtain the (8E,10Z)-1-halo-8,10-pentadecadiene (1) with a good yield and a high purity, because there are only a few known examples of the coupling of a Grignard reagent with a dihalomethane, where the desired coupling products are not obtained with a good yield.

Accordingly, we thought that suitable combinations of the starting materials for preparing the (8E,10Z)-1-halo-8,10-pentadecadiene (1) were a (4E,6Z)-1-halo-4,6-undecadiene and a 1,4-dihalobutane, where n=3, and a (5E,7Z)-1-halo-5,7-dodecadiene and a 1,3-dihalopropane, where n=4.

Accordingly, the inventors have first tried to prepare the (8E,10Z)-1-halo-8,10-pentadecadiene (1) by the coupling reaction between a (5E,7Z)-5,7-dodecadienyl magnesium halide prepared from a (5E,7Z)-1-halo-5,7-dodecadiene with n=4 and 1,3-dihalopropane.

Then, it has been turned out that, during the preparation of the (5E,7Z)-5,7-dodecadienyl magnesium halide from the (5E,7Z)-1-halo-5,7-dodecadiene, byproducts such as 6-chloro-1-cyclopentyl-3-butyl-1-hexene and 1-chloro-4-cyclopentyl-5-decene are formed, which are presumably formed via intramolecular cyclization of the (5E,7Z)-5,7-dodecadienyl magnesium halide and subsequent coupling with the 1,3-dihalopropane. Thus, the desired (8E,10Z)-1-halo-8,10-pentadecadiene is obtained only in a low yield.

As the results of the investigation, the inventors have found that the (8E,10Z)-1-halo-8,10-pentadecadiene (1) can be produced with a high yield and high purity by the coupling reaction of the (4E,6Z)-4,6-undecadienyl magnesium halide prepared from the (4E,6Z)-1-halo-4,6-undecadiene (n=3) with the 1,4-dihalobutane, and have successfully established an advantageous synthetic route in view of the yield and ease of purification.

As described above, it has been newly discovered that an appropriate selection of the chain length of the 1-haloalkadiene is critical for the coupling reaction of the alkadienyl magnesium halide prepared from the 1-haloalkadiene with the dihaloalkane, and, otherwise, unexpected reactions may progress.

First, here described is the step of preparing an (8E,10Z)-1-halo-8,10-pentadecadiene of the general formula (1) by a coupling reaction of a (4E,6Z)-4,6-undecadienyl magnesium halide prepared from a (4E,6Z)-1-halo-4,6-undecadiene of the general formula (5) with a 1,4-dihalobutane of the general formula (6), in the process for preparing (9E,11Z)-9,11-hexadecadienal.

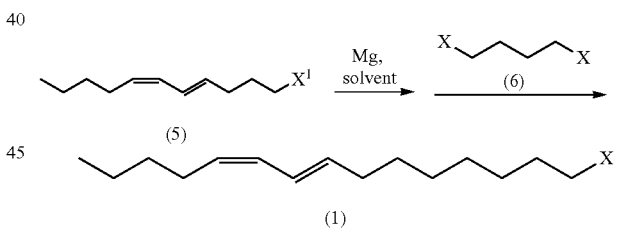

wherein X and $X^1$ are as defined above.

Specific examples of the (4E,6Z)-1-halo-4,6-undecadiene (5) include (4E,6Z)-1-chloro-4,6-undecadiene, (4E,6Z)-1-bromo-4,6-undecadiene, and (4E,6Z)-1-iodo-4,6-undecadiene, with (4E,6Z)-1-chloro-4,6-undecadiene or (4E,6Z)-1-bromo-4,6-undecadiene being preferred in view of the ease of preparing a Grignard reagent.

It should be noted that the (4E,6Z)-1-halo-4,6-undecadiene (5) may be prepared by, for example, a Wittig reaction of a (2E)-6-halo-2-hexenal with an ylide derived from a 1-halopentane.

The (4E,6Z)-4,6-undecadienyl magnesium halide may be prepared from the (4E,6Z)-1-halo-4,6-undecadiene (5) by subjecting the (4E,6Z)-1-halo-4,6-undecadiene (5) to a reaction with magnesium in a solvent.

The amount of magnesium to be used in the preparation of the (4E,6Z)-4,6-undecadienyl magnesium halide from the (4E,6Z)-1-halo-4,6-undecadiene (5) may range from 1.0 to 2.0 gram atoms (24.3 to 48.6 g) per mol of the (4E,6Z)-1-halo-4,6-undecadiene (5), for completion of the reaction.

Examples of the solvent to be used in the preparation of the (4E,6Z)-4,6-undecadienyl magnesium halide from the (4E,6Z)-1-halo-4,6-undecadiene (5) include ether solvents, such as tetrahydrofuran, diethyl ether and 4-methyltetrahydropyran; and hydrocarbon solvents, such as toluene, xylene and hexane. Tetrahydrofuran is preferred in view of the reaction rate of the Grignard reagent formation.

The amount of the solvent to be used may range preferably from 100 to 600 g per mol of the (4E,6Z)-1-halo-4,6-undecadiene (5), in view of the reactivity.

The reaction temperature in the preparation of the (4E,6Z)-4,6-undecadienyl magnesium halide from the (4E,6Z)-1-halo-4,6-undecadiene (5) may vary, depending on the type of the solvent to be used. It ranges preferably from 30 to 120° C. in view of the reactivity.

The duration of the reaction for the preparation of the (4E,6Z)-4,6-undecadienyl magnesium halide from the (4E,6Z)-1-halo-4,6-undecadiene (5) may vary, depending on the type of the solvent or a scale of the reaction system. It ranges preferably from 1 to 30 hours in view of the reactivity.

In the general formula (6) for the 1,4-dihalobutanes, X may be the same or different at each occurrence and is a halogen atom, examples of which include chlorine, bromine and iodine atoms.

Illustrative combinations of X groups include chlorine and chlorine atoms, chlorine and bromine atoms, chlorine and iodine atoms, bromine and bromine atoms, bromine and iodine atoms, and iodine and iodine atoms.

Specific examples of the 1,4-dihalobutane (6) include 1,4-dichlorobutane, 1-bromo-4-chlorobutane, 1-chloro-4-iodobutane, 1,4-dibromobutane, 1-bromo-4-iodobutane and 1,4-diiodobutane. 1-Bromo-4-chlorobutane and 1-chloro-4-iodobutane are preferred in view of the suppression of byproduct formation. Any of a commercially available or synthesized 1,4-dihalobutane (6) may be used.

The amount of the 1,4-dihalobutane (6) to be used may range preferably from 1.0 to 10.0 mol, more preferably from 1.0 to 3.0 mol, per mol of the (4E,6Z)-1-halo-4,6-undecadiene (5), in view of the reactivity.

In a case where two different X groups are used, the coupling reaction may be conducted so that the reaction with X group of a higher reactivity proceeds preferentially by appropriately selecting the catalyst and the reaction temperature as described later. For example, when the combination of chlorine and bromine atoms or of chlorine and iodine atoms is used as the different X groups in the 1,4-dihalobutane (6), a product having a chlorine atom as the X group in the general formula (1) can be obtained. When the combination of bromine and iodine atoms is used as the different X groups in the 1,4-dihalobutane (6), a product having a bromine atom as the X group in the general formula (1) can be obtained.

A catalyst may be used for the coupling reaction, if necessary, in view of the reactivity.

Examples of the catalyst for the coupling reaction include copper (I) halides, such as cuprous chloride, cuprous bromide and cuprous iodide; copper (I) compounds, such as cuprous cyanide and cuprous oxide; copper (II) halides, such as cupric chloride, cupric bromide and cupric iodide; and copper (II) compounds, such as cupric cyanide, cupric oxide, and dilithium tetrachlorocuprate. Copper halides such as cuprous iodide are preferred in view of the reactivity.

For an economical reason, the amount of the catalyst to be used may range preferably from 0.003 to 0.300 mol, more preferably 0.003 to 0.030 mol, per mol of the (4E,6Z)-1-halo-4,6-undecadiene (5).

In the coupling reaction, the catalyst is preferably used in combination with a cocatalyst. Examples of the cocatalyst include phosphorus compounds, in particular trialkyl phosphites having 3 to 9 carbon atoms, such as triethyl phosphite; and triarylphosphines having 18 to 21 carbon atoms, such as triphenylphosphine. In view of the reactivity, triethyl phosphite is preferred.

The amount of the cocatalyst to be used may range preferably from 0.001 to 0.500 mol, more preferably 0.001 to 0.050 mol, per mol of the (4E,6Z)-1-halo-4,6-undecadiene (5).

Examples of the solvent to be used in the coupling reaction include ether solvents, such as tetrahydrofuran, diethyl ether and 4-methyltetrahydropyran; and hydrocarbon solvents, such as toluene, xylene and hexane. Tetrahydrofuran is preferred in view of the reactivity.

The amount of the solvent to be used may range preferably from 50 to 300 g, per mol of the (4E,6Z)-1-halo-4,6-undecadiene (5), in view of the reactivity.

The temperature for the coupling reaction may range preferably from 0 to 30° C. in view of the reactivity.

The duration of the coupling reaction may vary, depending on a scale of the reaction system. It ranges preferably from 0.1 to 10 hours in view of the reactivity.

Specific examples of the (8E,10Z)-1-halo-8,10-pentadecadiene (1) include (8E,10Z)-1-chloro-8,10-pentadecadiene, (8E,10Z)-1-bromo-8,10-pentadecadiene, and (8E,10Z)-1-iodo-8,10-pentadecadien. (8E,10Z)-1-Chloro-8,10-pentadecadiene and (8E,10Z)-1-bromo-8,10-pentadecadiene are preferred in view of the ease of preparing a Grignard reagent.

Next, there will be described the step of conducting a nucleophilic substitution reaction between a Grignard reagent derived from an (8E,10Z)-1-halo-8,10-pentadecadiene of the general formula (1) and an orthoformate ester of the general formula (2) to prepare a (9E,11Z)-1,1-dialkoxy-9,11-hexadecadiene of the general formula (3), in the process for preparing (9E,11Z)-9,11-hexadecadienal.

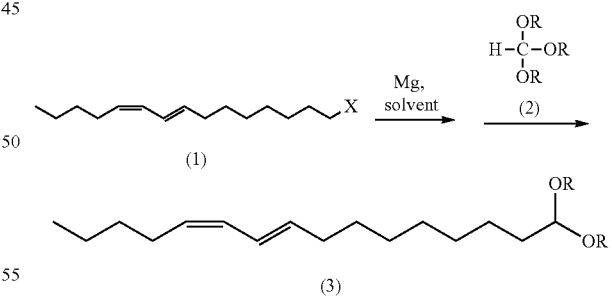

The (8E,10Z)-8,10-pentadecadienyl magnesium halide may be prepared from an (8E,10Z)-1-halo-8,10-pentadecadiene (1) by subjecting the (8E,10Z)-1-halo-8,10-pentadecadiene (1) to a reaction with magnesium in a solvent.

The amount of magnesium to be used for the preparation of the (8E,10Z)-8,10-pentadecadienyl magnesium halide from the (8E,10Z)-1-halo-8,10-pentadecadiene (1) may range preferably from 1.0 to 2.0 gram atoms (24.3 to 48.6 g) per mol of the (8E,10Z)-1-halo-8,10-pentadecadiene (1) for completion of the reaction.

Examples of the solvent to be used for the preparation of the (8E,10Z)-8,10-pentadecadienyl magnesium halide from the (8E,10Z)-1-halo-8,10-pentadecadiene (1) include ether solvents, such as tetrahydrofuran, diethyl ether and 4-methyltetrahydropyran; and hydrocarbon solvents, such as toluene, xylene and hexane. Tetrahydrofuran is preferred in view of the reaction rate of the Grignard reagent formation.

The amount of the solvent to be used may range preferably from 100 to 600 g per mol of the (8E,10Z)-1-halo-8,10-pentadecadiene (1), in view of the reactivity.

The reaction temperature for the preparation of the (8E,10Z)-8,10-pentadecadienyl magnesium halide from the (8E,10Z)-1-halo-8,10-pentadecadiene (1) may vary, depending on the type of the solvent to be used. It ranges preferably from 30 to 120° C. in view of the reactivity.

The duration of the reaction for the preparation of the (8E,10Z)-8,10-pentadecadienyl magnesium halide from the (8E,10Z)-1-halo-8,10-pentadecadiene (1) may vary, depending on the type of the solvent or a scale of the reaction system. It ranges preferably from 1 to 30 hours in view of the reactivity.

In the general formula (2) for the orthoformate ester, R may be the same or different at each occurrence and is an alkyl group having 1 to 6 carbon atoms, preferably 1 to 3 carbon atoms. Examples thereof include linear alkyl groups, such as methyl, ethyl, n-propyl, n-butyl, n-pentyl and n-hexyl; and branched alkyl groups, such as isopropyl. Preferably, the three R groups are the same, in view of the availability and the purification after the reaction.

Specific examples of the orthoformate ester (2) include orthoformate esters having linear alkyl groups, such as methyl orthoformate, ethyl orthoformate, propyl orthoformate, butyl orthoformate, pentyl orthoformate and hexyl orthoformate; and orthoformate esters having branched alkyl groups, such as isopropyl orthoformate. Methyl orthoformate and ethyl orthoformate are preferred in view of the availability. Any of a commercially available or synthesized orthoformate ester (2) may be used.

The amount of the orthoformate ester (2) to be used may range preferably from 1.0 to 3.0 mol per mol of the (8E,10Z)-1-halo-8,10-pentadecadiene (1), in view of the reactivity.

Examples of the solvent to be used in the coupling reaction include hydrocarbon solvents, such as toluene, xylene and hexane; and ether solvents, such as tetrahydrofuran, diethyl ether and 4-methyltetrahydropyran Tetrahydrofuran and toluene are preferred in view of the reactivity.

The amount of the solvent to be used may range preferably from 100 to 800 g per mol of the (8E,10Z)-1-halo-8,10-pentadecadiene (1), in view of the reactivity.

The temperature in the nucleophilic substitution reaction may range preferably from 75 to 130° C. to allow the reaction to proceed smoothly and to prevent evaporation of the solvent.

The duration of the nucleophilic substitution reaction may vary, depending on the type of the solvent or a scale of the reaction system. It ranges preferably from 3 to 35 hours in view of the reactivity.

In the general formula (3) for the (9E,11Z)-1,1-dialkoxy-9,11-hexadecadiene, R is as defined above for the orthoformate ester (2).

Specific examples of the (9E,11Z)-1,1-dialkoxy-9,11-hexadecadiene of the general formula (3) include (9E,11Z)-1,1-dimethoxy-9,11-hexadecadiene, (9E,11Z)-1,1-dithoxy-9,11-hexadecadiene, (9E,11Z)-1,1-dipropoxy-9,11-hexadecadiene, and (9E,11Z)-1,1-diisopropoxy-9,11-hexadecadiene. (9E,11Z)-1,1-Dimethoxy-9,11-hexadecadiene and (9E,11Z)-1,1-diethoxy-9,11-hexadecadiene are preferred in view of the ease of production.

Next, there will be described the step of hydrolyzing the (9E,11Z)-1,1-dialkoxy-9,11-hexadecadiene (3) to obtain (9E,11Z)-9,11-hexadecadienal (4), in the process for preparing (9E,11Z)-9,11-hexadecadienal.

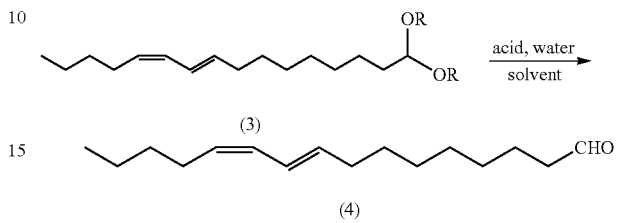

The hydrolysis of the (9E,11Z)-1,1-dialkoxy-9,11-hexadecadiene (3) may be carried out using, for example, an acid, water, and, if necessary, a solvent.

Examples of the acid that may be used in the hydrolysis include inorganic acids, such as hydrochloric acid, hydrobromic acid, nitric acid, and sulfuric acid; and p-toluenesulfonic acid, trifluoroacetic acid, acetic acid, formic acid, oxalic acid, trimethylsilyl iodide, and titanium tetrachloride. Hydrochloric acid, sulfuric acid, p-toluene sulfonic acid, acetic acid, formic acid, oxalic acid and trimethylsilyl iodide are preferred in view of the reactivity.

The amount of the acid to be used may range preferably from 0.01 to 10.00 mol per mol of the (9E,11Z)-1,1-dialkoxy-9,11-hexadecadiene (3), in view of the reactivity.

The amount of water to be used may range preferably from 18 to 3,000 g per mol of the (9E,11Z)-1,1-dialkoxy-9,11-hexadecadiene (3), in view of the reactivity.

Examples of the solvent that may be used in the hydrolysis include ether solvents, such as tetrahydrofuran, diethyl ether and 4-methyltetrahydropyran; hydrocarbon solvents, such as toluene, xylene and hexane; polar solvents, such as N,N-dimethylformamide, N,N-dimethylacetamide, acetonitrile, dichloromethane and chloroform; and alcoholic solvents, such as methanol and ethanol. The optimum solvent may vary, depending on the type of the acid to be used. For example, when oxalic acid is used as the acid, tetrahydrofuran is preferred in view of the reactivity.

The amount of the solvent to be used may range preferably from 0 to 3,000 g per mol of the (9E,11Z)-1,1-dialkoxy-9,11-hexadecadiene (3), in view of the reactivity.

The reaction temperature in the hydrolysis may vary, depending on the type of the solvent to be used. It ranges preferably from 5 to 150° C. in view of the reactivity.

The duration of the hydrolysis may vary, depending on the type of the solvent or a scale of the reaction system. It ranges preferably from 1 to 10 hours in view of the reactivity.

As described above, an efficient process for preparing (9E,11Z)-9,11-hexadecadienal (4), sex pheromone of the pecan nut casebearer (*Acrobasis nuxvorella*), is provided.

EXAMPLES

The invention will be further described with reference to the following Synthesis Example and Examples. It should be construed that the invention is not limited to or by Examples.

Synthesis Example 1

Preparation of (4E,6Z)-1-chloro-4,6-undecadiene (5: X=Cl)

To a reactor were charged 1-bromopentane (299 g, 1.94 mol), triphenylphosphine (519 g, 1.94 mol) and N,N-dimethylformamide (436 g), and the resulting mixture was stirred at 110 to 115° C. for 6 hours to prepare pentyltriphenylphosphonium bromide. The reaction mixture was cooled to 20 to 30° C., to which was added tetrahydrofuran (1870 g). Then, it was cooled to 0 to 10° C., to which was added potassium t-butoxide (224 g, 1.94 mol). It was stirred at 10 to 15° C. for 30 minutes, and then (2E)-6-chloro-2-hexenal (263 g, 1.41 mol) was added dropwise at −5 to 5° C. After completion of the dropwise addition, the reaction mixture was stirred for 3 hours, and then the reaction was stopped by the addition of water (1040 g) to the reaction mixture. After removal of the aqueous layer by liquid-liquid separation, the organic layer was concentrated by evaporating the solvent under vacuum. Then, hexane (1150 g) was added to cause precipitation of triphenylphosphineoxide, which was then removed by filtration. The filtrate was concentrated by evaporating the solvent under vacuum, and the resulting concentrate was subjected to distillation under vacuum to obtain (4E,6Z)-1-chloro-4,6-undecadiene (5: X=Cl) (297 g, 1.26 mol) with a yield of 90.0%.

Characterization of (4E,6Z)-1-chloro-4,6-undecadiene (5: X=Cl)

[NMR Spectra] $^1$H-NMR (500 MHz, CDCl$_3$): δ0.91 (3H, t, J=6.9 Hz), 1.30-1.40 (4H, m), 1.87 (2H, tt, J=6.9, 6.9 Hz), 2.17 (2H, dt, J=6.9, 6.9 Hz), 2.26 (2H, dt, J=6.9, 6.9 Hz), 3.54 (2H, t, J=6.9 Hz), 5.34 (1H, dt, J=10.7, 6.9 Hz), 5.60 (1H, dt, J=15.3, 6.9 Hz), 5.94 (1H, dd, J=10.7, 10.7 Hz), 6.36 (1H, dd, J=15.3, 10.7 Hz); $^{13}$C-NMR (75.6 MHz, CDCl$_3$): 13.93, 22.28, 27.39, 29.88, 31.83, 32.12, 44.35, 127.01, 128.15, 130.97, 131.89

[Mass Spectrum] EI-Mass Spectrum (70 eV): m/z 186 (M+), 157, 143, 130, 107, 95, 81, 67, 55, 41, 27

[IR Absorption Spectrum] (NaCl): νmax 3018, 2956, 2928, 2856, 1464, 1377, 1309, 983, 949, 728, 653

Example 1

Preparation of (8E,10Z)-1-chloro-8,10-pentadecadiene (1: X=Cl)

To a reactor were charged magnesium (17.8 g, 0.733 gram atoms) and tetrahydrofuran (198 g), and the resulting mixture was stirred at 60 to 65° C. for 30 minutes. Then, (4E,6Z)-1-chloro-4,6-undecadiene (5: X=Cl) (124 g, 0.667 mol) was added dropwise at 60 to 70° C., and the resulting mixture was stirred at 70 to 75° C. for 6 hours to prepare (4E,6Z)-4,6-undecadienyl magnesium chloride. To another reactor were charged cuprous iodide (1.27 g, 0.00667 mol), triethyl phosphite (2.66 g, 0.0160 mol), 1-bromo-4-chlorobutane (131 g, 0.767 mol) and tetrahydrofuran (66.1 g), and the resulting mixture was stirred at 0 to 5° C. for 30 minutes. Then, the solution of (4E,6Z)-4,6-undecadienyl magnesium chloride in tetrahydrofuran as prepared above was added dropwise at 5 to 15° C. After completion of the dropwise addition, the resulting reaction mixture was stirred at 5 to 10° C. for 2 hours, and then the reaction was stopped by the addition of ammonium chloride (6.29 g), 20 wt % aqueous hydrogen chloride (10.1 g) and water (176 g) to the reaction mixture. After removal of the aqueous layer by liquid-liquid separation, the organic layer was concentrated by evaporating the solvent under vacuum, and the resulting concentrate was subjected to distillation under vacuum to obtain (8E,10Z)-1-chloro-8,10-pentadecadiene (1: X=Cl) (145 g, 0.596 mol) with a yield of 89.3%.

Characterization of (8E,10Z)-1-chloro-8,10-pentadecadiene (1: X=Cl)

[NMR Spectra] $^1$H-NMR (500 MHz, CDCl$_3$): δ0.91 (3H, t, J=6.9 Hz), 1.29-1.46 (12H, m), 1.77 (2H, tt, J=6.9, 6.9 Hz), 2.10 (2H, dt, J=6.9, 6.9 Hz), 2.16 (2H, dt, J=6.9, 6.9 Hz), 3.53 (2H, t, J=6.9 Hz), 5.31 (1H, dt, J=10.7, 7.7 Hz), 5.64 (1H, dt, J=15.3, 6.9 Hz), 5.94 (1H, dd, J=10.7, 10.7 Hz), 6.30 (1H, dd, J=15.3, 10.7 Hz); $^{13}$C-NMR (75.6 MHz, CDCl$_3$): 13.94, 22.30, 26.80, 27.37, 28.72, 28.98, 29.25, 31.88, 32.59, 32.78, 45.10, 125.71, 128.52, 130.13, 134.38

[Mass Spectrum] EI-Mass Spectrum (70 eV): m/z 242 (M+), 158, 144, 123, 109, 95, 81, 67, 55, 41, 27

[IR Absorption Spectrum] (NaCl): νmax 3018, 2955, 2928, 2856, 1465, 1377, 1309, 982, 948, 727, 654

Example 2

Preparation of (9E,11Z)-1,1-diethoxy-9,11-hexadecadiene (3: R=C$_2$H$_5$)

To a reactor were charged magnesium (7.82 g, 0.322 gram atoms) and tetrahydrofuran (87.8 g), and the resulting mixture was stirred at 60 to 65° C. for 30 minutes. Then, (8E,10Z)-1-chloro-8,10-pentadecadiene (1: X=Cl) (71.1 g, 0.293 mol) was added dropwise at 60 to 70° C., and then the resulting mixture was stirred at 70 to 75° C. for 2 hours to prepare (8E,10Z)-8,10-pentadecadienyl magnesium chloride. Then, toluene (136 g) and tritriethyl orthoformate (56.4 g, 0.380 mol) were added to the reactor at 75 to 85° C., and the resulting mixture was stirred at 90 to 100° C. for 17 hours. It was cooled to 0 to 10° C., and then 20 wt % aqueous hydrogen chloride (40.5 g), water (43.9 g) and acetic acid (8.08 g) were added to the reaction mixture. After removal of the aqueous layer by liquid-liquid separation of the resulting reaction mixture, the organic layer was washed with an aqueous solution of 8 wt % sodium hydroxide (48.4 g). The organic layer was concentrated by evaporating the solvent under vacuum, and the resulting concentrate was subjected to distillation under vacuum to obtain (9E,11Z)-1,1-diethoxy-9,11-hexadecadiene (3: R=C$_2$H$_5$) (67.1 g, 0.216 mol) with a yield of 73.8%.

Characterization of (9E,11Z)-1,1-diethoxy-9,11-hexadecadiene (3: R=C$_2$H$_5$)

[NMR Spectra] $^1$H-NMR (500 MHz, CDCl$_3$): δ0.90 (3H, t, J=7.3 Hz), 1.20 (6H, t, J=7.3 Hz), 1.29-1.39 (14H, m), 1.57-1.62 (2H, m), 2.08 (2H, dt, J=7.3, 7.3 Hz), 2.16 (2H, dt, J=7.3, 7.3 Hz), 3.45-3.51 (2H, m), 3.60-3.66 (2H, m), 4.47 (1H, t, J=5.8 Hz), 5.29 (1H, dt, J=10.7, 7.3 Hz), 5.64 (1H, dt, J=14.9, 7.3 Hz), 5.93 (1H, dd, J=10.7, 10.7 Hz), 6.29 (1H, dd, J=14.9, 10.7 Hz); $^{13}$C-NMR (75.6 MHz, CDCl$_3$): 13.94, 15.33 (2C), 22.30, 24.73, 27.36, 29.13, 29.40 (2C), 31.88, 32.84, 33.57, 43.87, 60.78 (2C), 102.93, 125.60, 128.56, 130.02, 134.57

[Mass Spectrum] EI-Mass Spectrum (70 eV): m/z 264 (M+−46), 220, 175, 149, 121, 103, 85, 67, 47, 29

[IR Absorption Spectrum] (NaCl): νmax 3019, 2974, 2927, 2856, 1465, 1374, 1344, 1128, 1062, 982, 948, 843, 725

Example 3

Preparation of (9E,11Z)-9,11-hexadecadienal (4)

To a reactor were charged (9E,11Z)-1,1-diethoxy-9,11-hexadecadiene (3: R=C$_2$H$_5$) (146 g, 0.469 mol), tetrahydrofuran (469 g), oxalic acid dihydrate (177 g, 1.41 mol) and water (469 g), and the resulting mixture was stirred at 60 to 65° C. for 3 hours. It was cooled to 40 to 50° C., and hexane (138 g) was added to the mixture. After removal of the aqueous layer by liquid-liquid separation of the resulting reaction mixture, the organic layer was washed with a solution of sodium chloride (4.27 g) and water (286 g). The organic layer was concentrated by evaporating the solvent under vacuum, and the resulting concentrate was subjected to distillation under vacuum to obtain (9E,11Z)-9,11-hexadecadienal (4) (93.0 g, 0.394 mol) with a yield of 83.9%.

Characterization of (9E,11Z)-9,11-hexadecadienal (4)

[NMR Spectra] $^1$H-NMR (500 MHz, CDCl$_3$): δ0.90 (3H, t, J=6.9 Hz), 1.29-1.41 (12H, m), 1.62 (2H, tt, J=7.3, 7.3 Hz), 2.08 (2H, dt, J=6.9, 6.9 Hz), 2.15 (2H, dt, J=7.3, 7.3 Hz), 2.41 (2H, td, J=7.3, 1.9 Hz), 5.29 (1H, dt, J=10.7, 6.9 Hz), 5.63 (1H, dt, J=14.9, 7.3 Hz), 5.93 (1H, dd, J=10.7, 10.7 Hz), 6.29 (1H, dd, J=14.9, 10.7 Hz), 9.75 (1H, t, J=1.9 Hz); $^{13}$C-NMR (75.6 MHz, CDCl$_3$): 13.92, 22.01, 22.28, 27.34, 28.93, 29.06, 29.16, 29.26, 31.86, 32.77, 43.85, 125.67, 128.51, 130.09, 134.38, 202.80

[Mass Spectrum] EI-Mass Spectrum (70 eV): m/z 236 (M+), 151, 135, 123, 109, 95, 81, 67, 55, 41, 29

[IR Absorption Spectrum] (NaCl): νmax 3018, 2927, 2855, 2714, 1727, 1465, 1410, 1102, 983, 949, 832, 726

The invention claimed is:

1. A process for preparing (9E,11Z)-9,11-hexadecadienal of the following formula (4):

(4)

said process comprising at least steps of:
conducting a nucleophilic substitution reaction between an (8E,10Z)-8,10-pentadecadienyl magnesium halide derived from an (8E,10Z)-1-halo-8,10-pentadecadiene of the following general formula (1):

(1)

wherein X is a halogen atom, and an orthoformate ester of the following general formula (2):

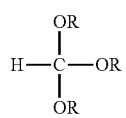
(2)

wherein R may be the same or different at each occurrence and is an alkyl group having 1 to 6 carbon atoms, to thereby prepare a (9E,11Z)-1,1-dialkoxy-9,11-hexadecadiene of the general formula (3):

(3)

wherein R may be the same or different at each occurrence and is an alkyl group having 1 to 6 carbon atoms; and
hydrolyzing the (9E,11Z)-1,1-dialkoxy-9,11-hexadecadiene (3) to obtain (9E,11Z)-9,11-hexadecadienal of the formula (4) shown above.

2. A process for preparing (9E,11Z)-9,11-hexadecadienal of the following formula (4):

(4)

said process comprising at least steps of:
conducting a nucleophilic substitution reaction between an (8E,10Z)-8,10-pentadecadienyl magnesium halide derived from an (8E,10Z)-1-halo-8,10-pentadecadiene of the following general formula (1):

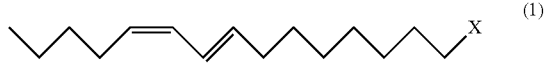
(1)

wherein X is a halogen atom, and an orthoformate ester of the following general formula (2):

(2)

wherein R may be the same or different at each occurrence and is an alkyl group having 1 to 6 carbon atoms, to thereby prepare a (9E,11Z)-1,1-dialkoxy-9,11-hexadecadiene of the general formula (3):

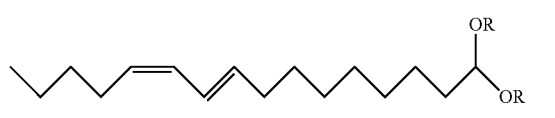
(3)

wherein R may be the same or different at each occurrence and is an alkyl group having 1 to 6 carbon atoms; and
hydrolyzing the (9E,11Z)-1,1-dialkoxy-9,11-hexadecadiene (3) to obtain (9E,11Z)-9,11-hexadecadienal of the formula (4) shown above, and further comprising steps of:

conducing a coupling reaction between a (4E,6Z)-4,6-undecadienyl magnesium halide derived from a (4E,6Z)-1-halo-4,6-undecadiene of the following general formula (5):

(5)

wherein $X^1$ is a halogen atom, and a 1,4-dihalobutane of the following general formula (6):

(6)

wherein X may be the same or different at each occurrence and is a halogen atom, to thereby prepare the (8E,10Z)-1-halo-8,10-pentadecadiene (1); and reacting the (8E,10Z)-1-halo-8,10-pentadecadiene (1) with magnesium to prepare the (8E,10Z)-8,10-pentadecadienyl magnesium halide.

* * * * *